United States Patent
Soga et al.

(10) Patent No.: US 9,978,573 B2
(45) Date of Patent: May 22, 2018

(54) METHOD OF CREATING SPRAY DEVICE FOR SHEATHLESS CE-MS, SPRAY DEVICE FOR SHEATHLESS CE-MS, AND SHEATHLESS CE-MS DEVICE

(71) Applicant: KEIO UNIVERSITY, Tokyo (JP)

(72) Inventors: Tomoyoshi Soga, Tsuruoka (JP); Akiyoshi Hirayama, Tsuruoka (JP); Hiroshi Abe, Tsuruoka (JP)

(73) Assignee: KEIO UNIVERSITY, Tokyo (JP)

( * ) Notice: Subject to any disclaimer, the term of this patent is extended or adjusted under 35 U.S.C. 154(b) by 0 days. days.

(21) Appl. No.: 15/552,918

(22) PCT Filed: Mar. 15, 2016

(86) PCT No.: PCT/JP2016/058131
§ 371 (c)(1),
(2) Date: Aug. 23, 2017

(87) PCT Pub. No.: WO2016/158380
PCT Pub. Date: Oct. 6, 2016

(65) Prior Publication Data
US 2018/0033599 A1 Feb. 1, 2018

(30) Foreign Application Priority Data
Apr. 1, 2015 (JP) ................. 2015-075494

(51) Int. Cl.
*H01J 49/00* (2006.01)
*H01J 49/04* (2006.01)
(Continued)

(52) U.S. Cl.
CPC .......... *H01J 49/045* (2013.01); *B01D 61/422* (2013.01); *G01N 27/44791* (2013.01); *H01J 49/0404* (2013.01)

(58) Field of Classification Search
CPC .. H01J 49/045; H01J 49/0404; B01D 61/422; G01N 27/44791
(Continued)

(56) References Cited

U.S. PATENT DOCUMENTS

| 5,993,633 A | 11/1999 | Smith et al. |
| 9,543,137 B2 * | 1/2017 | Apffel ................... G01N 35/08 |
| 2015/0311056 A1 * | 10/2015 | Dovichi ............ G01N 27/4473 250/282 |

FOREIGN PATENT DOCUMENTS

| JP | 2001-083119 A | 3/2001 |
| JP | 3341765 B1 | 11/2002 |

(Continued)

OTHER PUBLICATIONS

May 31, 2016 International Search Report issued in International Patent Application No. PCT/JP2016/058131.
(Continued)

*Primary Examiner* — Michael Maskell
(74) *Attorney, Agent, or Firm* — Oliff PLC

(57) ABSTRACT

Processing a capillary distal end into acute-angle, an electrophoretic liquid passing hole through which electrophoretic liquid pass is opened in a flexible insulating plate. An electrodialysis-membrane is bonded covering the electrophoretic liquid passing hole; the capillary is securely bonded to the insulating plate portion with no gap therebetween, the portion excluding electrophoretic liquid passing hole on the electrodialysis top-membrane. A crack forms at the capillary portion at the electrophoretic liquid passing hole, with the capillary entirely secured to the insulating plate except portion at the electrophoretic liquid passing hole. The capillary is securely bonded to the insulating plate; reservoir stores electrophoretic liquid on the insulating plate-side to which the capillary is unsecured. An electrode insertion hole into which an electrode is inserted opened in the reservoir (Continued)

upper portion; the electrode is securely inserted into the electrode insertion hole. By this, high-sensitivity measurement is using a spray device for sheathless CE-MS.

9 Claims, 7 Drawing Sheets

(51) Int. Cl.
  *G01N 27/447* (2006.01)
  *B01D 61/42* (2006.01)
(58) Field of Classification Search
  USPC .................................. 250/281, 282, 288
  See application file for complete search history.

(56) References Cited

FOREIGN PATENT DOCUMENTS

| | | |
|---|---|---|
| JP | 4385171 B1 | 12/2009 |
| WO | 2015/197072 A1 | 12/2015 |

OTHER PUBLICATIONS

Ping Cao et al. "A Novel Sheathless Interface for Capillary Electrophoresis / Electrospray Ionization Mass Spectrometry Using an in-Capillary Electrode". Journal of American Society for Mass Spectrometry, vol. 8, 1997, pp. 561-564.

Zoltán Kele et al. "Design and Performance of a Sheathless Capillary Electrophoresis / Mass Spectrometry Interface by Combining Fused-Silica Capillaries With Gold-Coated Nanoelectrospray Tips". Rapid Communications in Mass Spectrometry, vol. 19, 2005, pp. 881-885.

Lian-Hua Shi et al. "A Sheathless CE/ESI-MS Interface With an Ionophore Membrane-Packed Electro-Conduction Channel". Electrophoresis, vol. 30, 2009, pp. 1661-1669.

Klaus Faserl et al. "Optimization and Evaluation of a Sheathless Capillary Electrophoresis-Electrospray Ionization Mass Spectrometry Platform for Peptide Analysis: Comparison to Liquid Chromatography-Electrospray Ionization Mass Spectrometry". Analytical Chemistry, vol. 83, 2011, pp. 7297-7305.

Chen-Wen Whang et al. "Cellulose Acetate-Coated Porous Polymer Joint for Capillary Zone Electrophoresis". Analytical Chemistry, vol. 64, 1992, pp. 2461-2464.

Tomoyshi Soga et al. "Quantitative Metabolome Analysis Using Capillary Electrophoresis Mass Spectrometry". Journal of Proteome Research, vol. 2, 2003, pp. 488-494.

Tomoyoshi Soga et al. "Differential Metabolomics Reveals Ophthalmic Acid as an Oxidative Stress Biomarker Indicating Hepatic Glutathione Consumption". The Journal of Biological Chemistry, vol. 281, No. 24, Jun. 16, 2006, pp. 16768-16776.

Junhua Wang et al. "Enhanced Neuropeptide Profiling Via Capillary Electrophoresis Off-Line Coupled With Maldi FTMS". Analytical Chemistry, vol. 80, 2008, pp. 6168-6177.

\* cited by examiner

METHOD OF CREATING SPRAY DEVICE FOR SHEATHLESS CE-MS, SPRAY DEVICE FOR SHEATHLESS CE-MS, AND SHEATHLESS CE-MS DEVICE

TECHNICAL FIELD

The present invention relates to a method of creating a spray device for sheathless CE (Capillary Electrophoresis)-MS (Mass Spectrometry), a spray device for sheathless CE-MS, and a sheathless CE-MS device, and more particularly to a method of creating a spray device for sheathless CE-MS which is capable of measuring compounds with high sensitivity, a spray device for sheathless CE-MS created, for example, by the creating method, and a sheathless CE-MS device that is provided with the spray device.

BACKGROUND ART

One of metabolome measurement methods or a capillary electrophoresis-mass spectrometry (CE-MS) method is very effective for measurements of ionic metabolites in various biological samples and has a very high specificity because most objects to be measured will not overlap with those by the gas chromatography-mass spectrometry (GC-MS) method or the liquid chromatography-mass spectrometry (LC-MS) method.

In general, in the CE-MS, as shown in FIG. 1, for example, at the top portion of a stainless needle 12 built in an electrospray interface (ESI) spray (hereafter simply referred to as a spray) 10 called the nebulizer, a buffer electrophoretic liquid (hereafter simply referred to as the electrophoretic liquid or buffer) 16 coming out of a capillary 14 is mixed with a solution containing an organic solvent called a sheath liquid 18. Then, from outside thereof, a nebulizer gas, for example, a nitrogen gas for accelerating ionization by creating fine droplets is sprayed, thereby applying voltages for electrophoresis and ionizing metabolites in the electrophoretic liquid 16 (see Patent Literatures 1 to 3). The sheath liquid 18 enables stable measurements.

However, a big problem with the current CE-MS method employing the sheath liquid 18 is that the concentration sensitivity (the detection sensitivity when samples having the same concentration are measured) is inferior as compared with another metabolome analysis technique.

The reason why the sensitivity is degraded in the CE-MS method is because the electrophoretic liquid 16 coming out of the capillary 14 is mixed with the sheath liquid 18 at the tip portion of the aforementioned nebulizer (10), thereby causing the object being measured in the sample to be diluted. For example, in the measurement conditions typically employed by the inventors, the dilution factor was calculated. It was found that the dilution factor was about 200 times. Because, the flow rate of the electrophoretic liquid 16 was 50 nL/min, whereas the flow rate of the sheath liquid 18 was 10 µL/min.

Thus, if the metabolite can be less diluted by the sheath liquid 18 at the tip portion of the nebulizer (10), or if a sheathless measurement method is possible without using the sheath liquid 18, it can be expected that the concentration sensitivity in the CE-MS is increased to a maximum of 200 times.

In the sheathless method, the sensitivity can be expected to increase due to no dilution at the outlet of the capillary 14, whereas it is difficult to perform CE-MS measurements with stability because there is no sheath liquid 18. The sheathless CE-MS methods reported so far can be largely divided into three as below.

(1) As shown in FIG. 2, a method for electrophoresis in which a minute hole is opened on the capillary 14 to directly embed and secure with an adhesive 24 an electrode 22 in the capillary 14 (Non-Patent Literature 1).

(2) As shown in FIG. 3, a method for electrophoresis in which an electrically conductive metal (for example, gold) 26 is evaporated onto the outlet of the capillary 14 (Non-Patent Literature 2).

(3) A method in which while typical electrophoresis is being performed with an electrophoretic liquid reservoir provided at some midpoint of a capillary, a compound in the electrophoretic liquid is migrated off-line with the help of an electroosmotic flow (a liquid flow that naturally occurs when a voltage is applied) EOF (Non-Patent Literature 3).

CITATION LIST

Patent Literature

Patent Literature 1: Japanese Patent Application Laid-Open No. 2001-83119
Patent Literature 2: Japanese Patent No. 3341765
Patent Literature 3: Japanese Patent No. 4385171

Non-Patent Literature

Non-Patent Literature 1: Cao, P and Moini M, "A Novel Sheathless Interface for Capillary Electrophoresis/Electrospray Ionization Mass Spectrometry Using an In-capillary Electrode", J. Am. Soc. Mass Spectrom. 8, 561-564, 1997.

Non-Patent Literature 2: Kele Z., Ferenc G., Klement E., Toth G K., Janaky T., "Design and performance of a sheathless capillary electrophoresis/mass spectrometry interface by combining fused-silica capillaries with gold-coated nanoelectrospray tips", Rapid Commun. Mass Spectrom. 19, 881-885, 2005.

Non-Patent Literature 3: Shi L H., Jin Y X., Moon D C., Kim S K. and Park S R. "A sheathless CE/ESI-MS interface with an ionophore membrane-packed electro-conduction channel", Electrophoresis 30, 1661-1669, 2009.

Non-Patent Literature 4: Faserl K., Sarg B., Kremser L. and Lindner H. "Optimization and Evaluation of a Sheathless Capillary Electrophoresis-Electrospray Ionization Mass Spectrometry Platform for Peptide Analysis: Comparison to Liquid Chromatography-Electrospray Ionization Mass Spectrometry", Anal. Chem. 83, 7297-7305, 2011.

Non-Patent Literature 5: Whang C-W and Chen I-C. "Cellulose acetate-coated porous polymer joint for capillary zone electrophoresis", Anal. Chem., 64 (1992), 2461-2464.

Non-Patent Literature 6: Soga, T., Ohashi, Y., Ueno, Y., Naraoka, H., Tomita, M., and Nishioka, T., "Quantitative Metabolome Analysis Using Capillary Electrophoresis Mass Spectrometry", J. Proteome Res. 2, 488-494, 2003.

Non-Patent Literature 7: Soga, T., Baran, R., Suematsu M., Ueno, Y., Ikeda, S., Sakurakawa T., Kakazu, Y., Ishikawa, T., Robert, M., Nishioka, T., Tomita, M., "Differential Metabolomics Reveals Ophthalmic Acid As An Oxidative Stress Biomarker Indicating Hepatic Glutathione Consumption", J. Biol. Chem. 281, 16768-16776, 2006.

SUMMARY OF INVENTION

Technical Problem

However, in the methods (1) and (2), the spray is not stable due to oxygen and hydrogen that occur through electrolysis on the electrode, and thus measurements cannot be made successfully.

On the other hand, for the method (3), a product called CESI-MS is commercially available from AB SCIEX Inc.

As shown in FIG. 4, this interface achieves electrophoresis in a manner such that a distal end of about 3 cm of the capillary 14, which is 30 μm in inner diameter and 150 μm in outer diameter, is chemically processed with hydrofluoric acid to reduce the glass thickness down to about 5 μm as a porous distal end 15, thereby enabling ions in the electrophoretic liquid 16 to pass therethrough. FIG. 4 shows an electrophoretic liquid capillary 20 for supplying an electrophoretic liquid formed of an electrical conductivity liquid. What can pass through the porous distal end 15 is limited to hydrogen ions and hydroxide ions, and metabolite ions in a sample do not pass therethrough but are carried to the outlet of the capillary 14 and detected. This enables the sheathless CE-MS (Non-Patent Literature 4).

However, this device is very expensive, and the line-up of capillaries currently available is only those of an inner diameter of 30 μm.

On the other hand, disclosed in Non-Patent Literature 5 is that a crack is created on a capillary for CZE (capillary electrophoresis) so as to perform electrochemical detection in CE; however, this has not been thought to be applied to CE-MS.

The present invention has been made to solve the conventional problems. It is therefore an object of the present invention to provide a spray device which is less expensive and can be created in a simplified manner, and can accommodate capillaries of various inner diameters.

Solution to Problem

The present invention solves the aforementioned problems by a method of creating a spray device for sheathless CE-MS, the method including: a step of processing a distal end of a capillary to have an acute angle; a step of opening an electrophoretic liquid passing hole, through which an electrophoretic liquid can pass, in a flexible insulating plate; a step of bonding an electrodialysis membrane so as to cover the electrophoretic liquid passing hole; a step of securely bonding the capillary to a portion of the insulating plate with no gap therebetween, the portion excluding the electrophoretic liquid passing hole on top of the electrodialysis membrane; a step of forming a crack at a portion of the capillary at the electrophoretic liquid passing hole, the capillary being entirely secured to the insulating plate except a portion at the electrophoretic liquid passing hole; a step of entirely securely bonding the capillary to the insulating plate; a step of placing a reservoir for storing the electrophoretic liquid on a side of the insulating plate to which the capillary is not secured; a step of opening an electrode insertion hole, into which an electrode is inserted, in an upper portion of the reservoir; and a step of inserting and securing the electrode into the electrode insertion hole.

Here, the step of forming the crack can include: a step of scratching, with a cutter, a surface of the portion of the capillary at the electrophoretic liquid passing hole; and a step of deflecting the insulating plate to bend the capillary, thereby forming a crack at the portion at the electrophoretic liquid passing hole.

Furthermore, the insulating plate may be a plastic plate or a glass plate.

Furthermore, the electrodialysis membrane may be an ion exchange membrane.

Furthermore, the reservoir may be made of an insulator.

Furthermore, the cutter may also be a ceramic cutter.

Furthermore, the present invention provides a spray device for sheathless CE-MS, the spray device including: a capillary with a distal end processed to have an acute angle and with a crack formed at an intermediate portion; an insulating plate to which the capillary is securely bonded and in which an electrophoretic liquid passing hole for enabling an electrophoretic liquid to pass therethrough is formed at a portion having the crack formed; an electrodialysis membrane bonded onto the electrophoretic liquid passing hole of the insulating plate; a reservoir which is placed on a side of the insulating plate having the capillary not secured thereto and which stores the electrophoretic liquid; and an electrode which is inserted and secured to an upper portion of the reservoir.

Furthermore, the present invention also provides a sheathless CE-MS device including the aforementioned spray device.

Advantageous Effects of Invention

The present invention features a method of creating a novel spray device for sheathless CE-MS into which the technique for creating a fine hole of a capillary and the electrodialysis membrane are combined. The basic principle is an application of a method of (3) in [Background Art], the method for migrating a compound in an electrophoretic liquid off-line with the help of an electroosmotic flow EOF while an electrophoretic liquid reservoir is provided at some midpoint of the capillary so as to perform typical electrophoresis.

A capillary used for analysis is so fine as to have an inner diameter of a few tens of μm. The highly accurate coupling of the capillary requires to exercise great care under the microscope, leading to a lot of time and efforts. However, according to the present invention, for example, the capillary is secured to a flexible insulating plate or a plastic plate for example, and then the insulating plate is deflected to make a crack. This makes it possible to enable coupling with high accuracy while eliminating the need for a special device or tool. Furthermore, the shape of the distal end of the capillary is processed to have an acute angle so as to facilitate spraying. Furthermore, the electrodialysis membrane having a very low fractionated molecular weight (for example, a cutoff mass of 100 Da) is used, thereby minimizing the leakage of an object to be measured through the crack. This device makes it possible to generate electrolysis before the distal end of the sprayer to thereby prevent the disturbance of spray caused by the occurrence of a gas which was problematic with the conventional sheathless CE-MS. Thus, according to the present invention, particularly in the metabolome measurement of positive ions, it is possible to make measurements with several times to several hundred times high sensitivity as compared with the conventional method.

Furthermore, from the crack onward, the target compound is moved only by the electroosmotic flow, so that the longer the distance from the crack to the outlet of the capillary, the wider the peak shape will possibly become. For example, it is possible to minimize the peak difference by making the distance from the crack to the capillary outlet 2 cm or less. Furthermore, the capillary used in the spray device of the present invention is applicable to those of any inner diameters, and thus offers a high versatility.

DESCRIPTION OF EMBODIMENTS

Figure 1:
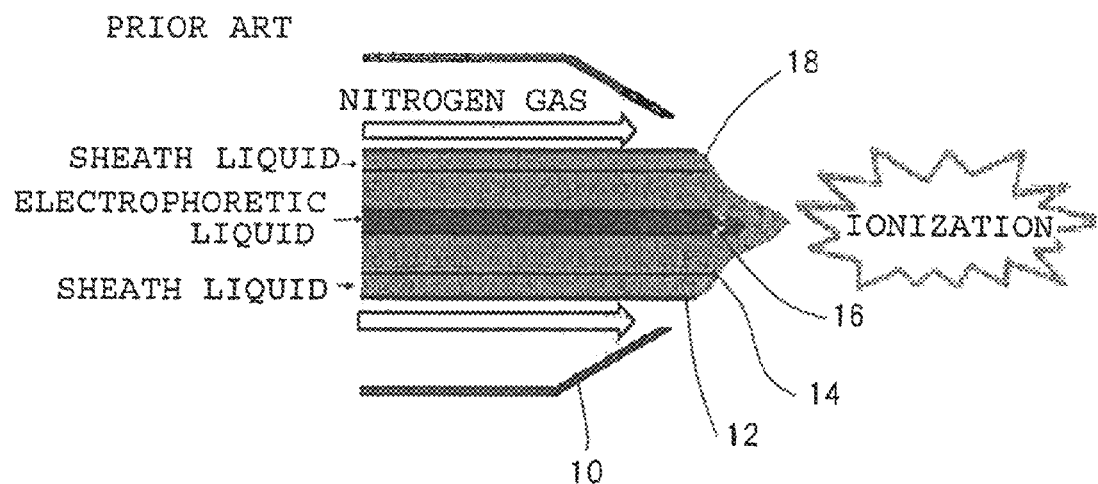
FIG. 1 is a cross-sectional view schematically illustrating the configuration of a nebulizer (spray) used for a conventional sheath flow CE-MS method.
Figure 2:
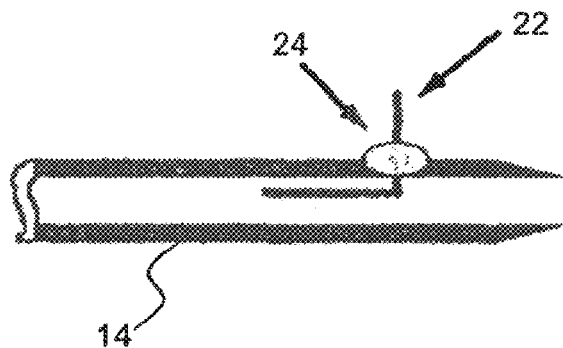
FIG. 2 is a cross-sectional view illustrating the distal end of a capillary as an example of a conventional sheathless interface.
Figure 3:
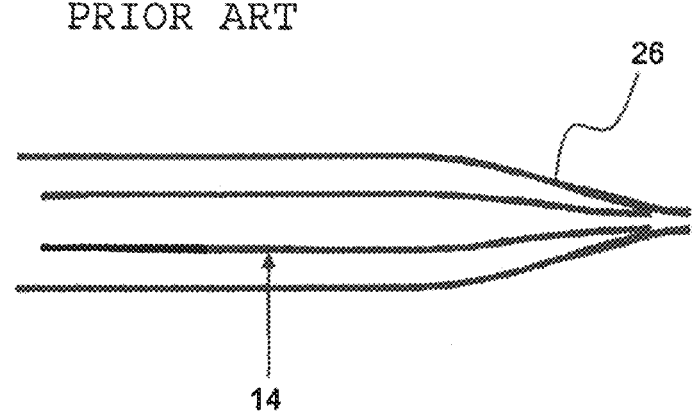
FIG. 3 is a cross-sectional view also illustrating the distal end of a capillary according to another example.
Figure 4:
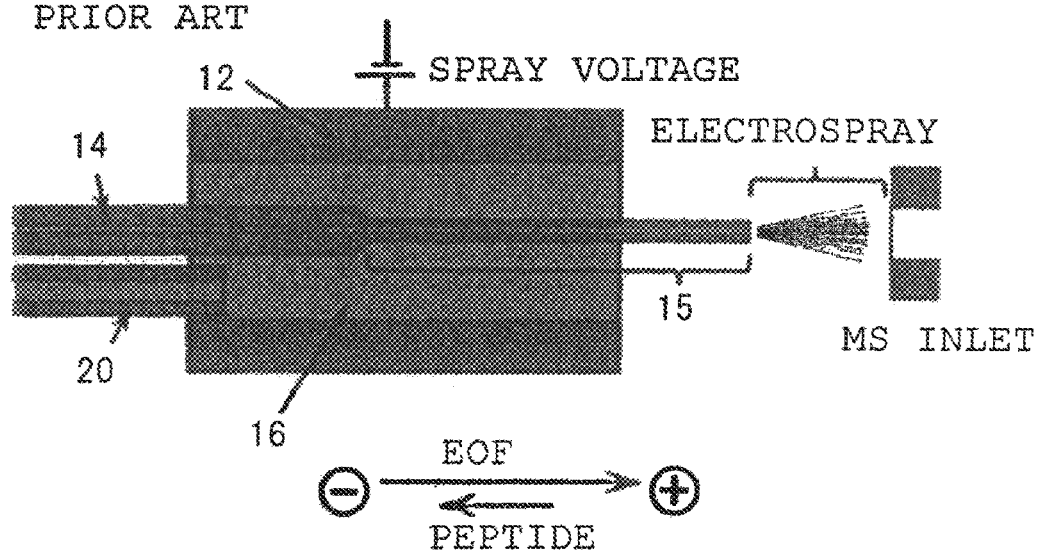
FIG. 4 is a cross-sectional view also illustrating the vicinity of the distal end of a capillary according to still another example.

Now, a description will be given of embodiments of the present invention in more detail by referring to the drawings. Note that the present invention will not be limited by the contents described in the embodiments and examples below. Furthermore, the constituent elements of the embodiments and examples described below include those which one skilled in the art can readily assume and are substantially the same, or those within a so-called equivalent range. Furthermore, those components disclosed in the embodiments and examples described below may be combined as appropriate or may also be selected to be used as appropriate.

Figure 5:
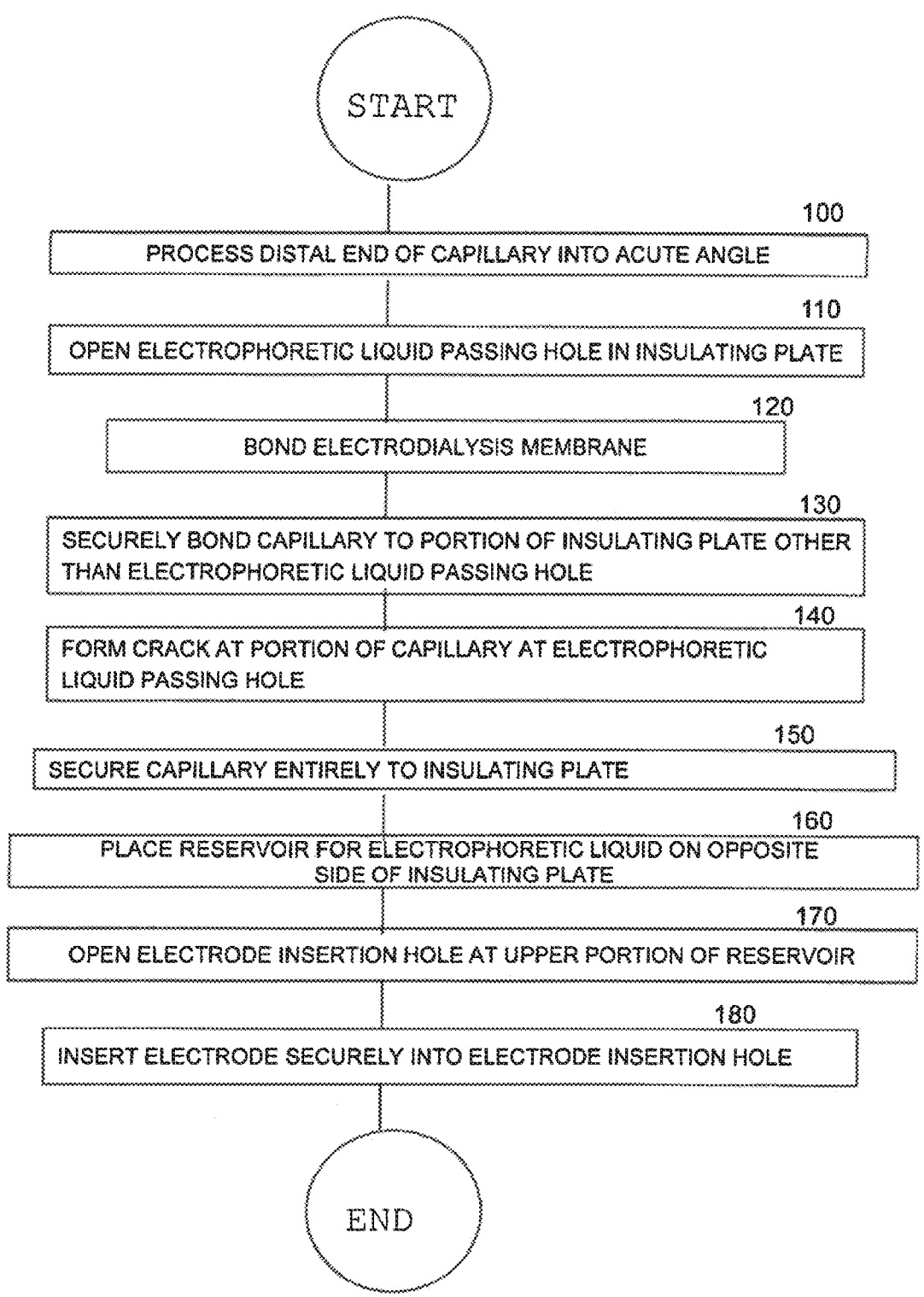
FIG. 5 is a flowchart indicative of the procedure for creating a spray device according to an embodiment of the present invention.

Now, referring to FIG. 5, a description will be given of a method of creating a spray device according to the present invention.

Figure 6:
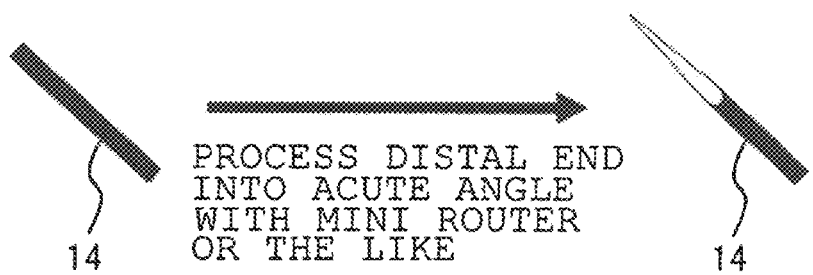
FIG. 6 is a perspective view also illustrating the distal end of a capillary being processed into an acute angle.

First of all, in step 100, for example, a polyimide film on the distal end of the capillary 14 is processed into an acute angle, for example, with a mini router (for example, made by PROXXON, MM 30GC, grindstone No. 150) as illustrated by way of example in FIG. 6. This step is required to perform spraying with stability. Here, as the capillary 14, it is possible to employ any capillary such as a coating capillary suggested by the inventor in Patent Literature 1 in addition to a typical fused silica capillary. Note that the method of processing the distal end of the capillary into an acute angle is not limited to the method with the mini router.

Figure 7A:
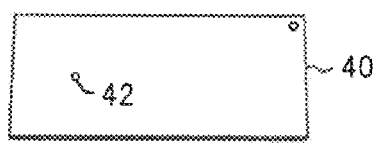
FIGS. 7A to 7G are perspective views also illustrating creating steps.

Then, in step 110, as illustrated in FIG. 7(A), an electrophoretic liquid passing hole 42 through which an electrophoretic liquid can pass is opened in a flexible insulating plate (for example, a plastic plate of acrylic resin having a thickness of about 2 mm) 40. Here, the size of the electrophoretic liquid passing hole 42 is preferably small. However, since too small holes may prevent the entry of the electrophoretic liquid therein due to the surface tension, the diameter thereof is preferably about 2 mm. Note that if a pipet is used to let the liquid in, the diameter can also be 1 mm.

As the type of the insulating plate 40, in addition to a plastic plate of an acrylic resin, it is possible to employ a plastic plate, which is not altered by an electrophoretic liquid used for CE-MS and slightly bent when a force is applied thereto, such as of polystyrene, polypropylene, polycarbonate, a PET resin, an AS resin, and PVC (vinyl chloride), or a glass plate which can be bent, for example, an ultra-thin flexible glass (for example, Willow Glass (registered trademark) by Corning (registered trademark)).

Figure 7B:
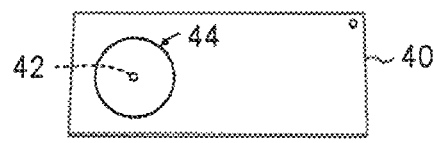

Then, in step 120, as illustrated in FIG. 7(B), for example, an electrodialysis membrane 44 formed of an ion exchange membrane (for example, a cellulose acetate membrane, 7427-CA 100, by HARVARD Apparatus) is bonded to thereby cover the electrophoretic liquid passing hole 42. Note that the type of the electrodialysis membrane 44 is not limited to the ion exchange membrane.

Figure 7C:
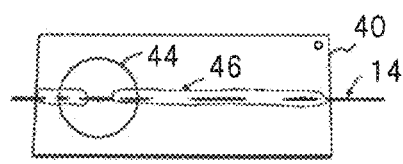

Then, in step 130, as illustrated in FIG. 7(C), the capillary 14 is securely bonded, with an adhesive 46, to a portion of the insulating plate 40 with no gap therebetween, the portion excluding the electrophoretic liquid passing hole 42.

Figure 7D:
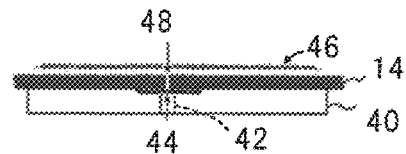

After the adhesive 46 is left as it is until it is hardened and the capillary 14 does not move anymore, in step 140, for example, a ceramic cutter is used to scratch a portion of the capillary 14 at the electrophoretic liquid passing hole 42 immediately above the electrodialysis membrane 44. Then, both ends of the insulating plate 40 are held so as to slightly deflect the insulating plate 40, thereby forming a crack 48 on the capillary 14 as illustrated in FIG. 7(D).

Figure 7E:
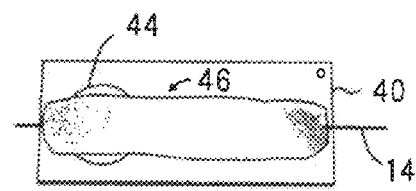

Then, the process proceeds to step 150, where as illustrated in FIG. 7(E), the adhesive 46 is applied to the entirety of the insulating plate 40 so as to entirely secure the capillary 14.

Figure 7F:
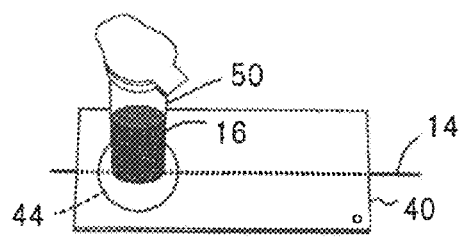

Then, the process proceeds to step 160, where as illustrated in FIG. 7(F), the insulating plate 40 is turned over, and a reservoir 50 for storing the electrophoretic liquid 16 is placed on the opposite side (the upper side in use) of the insulating plate 40. Here, the reservoir 50 can be formed of an arbitrary insulator, which is not altered by the electrophoretic liquid used for CE-MS, such as polypropylene or another plastic. Furthermore, as the electrophoretic liquid 16, any liquid can be used so long as the liquid is volatile, such as formic acid, acetic acid, ammonium formate, ammonium acetate, or ammonium carbonate.

Figure 7G:
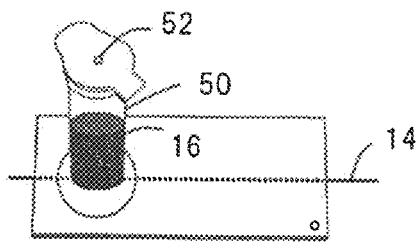

Then, the process proceeds to step 170, where as illustrated in FIG. 7(G), the reservoir 50 is provided on top thereof with an electrode insertion hole 52 opened for inserting an electrode therein. The diameter of the electrode insertion hole 52 is, for example, about 1 mm to conform to the size of the electrode.

Figure 8A:
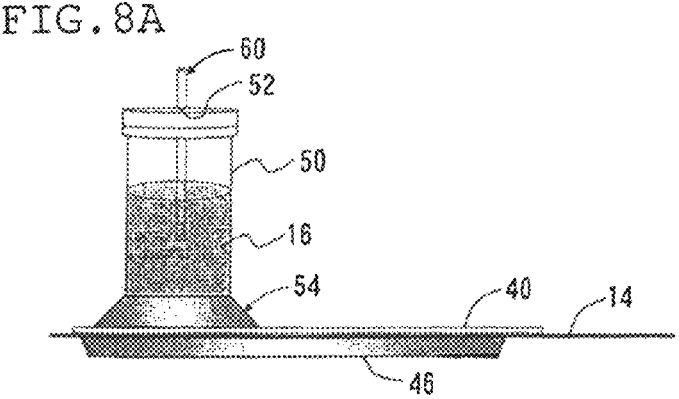
FIG. 8A is a front view.
Figure 8C:
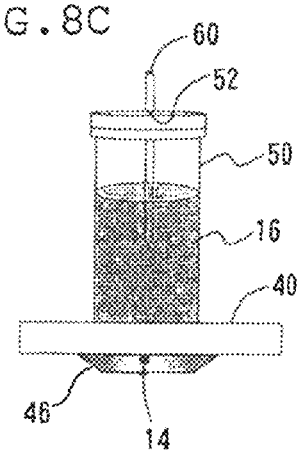
FIG. 8C is a side view illustrating a completed spray device.
Figure 8B:
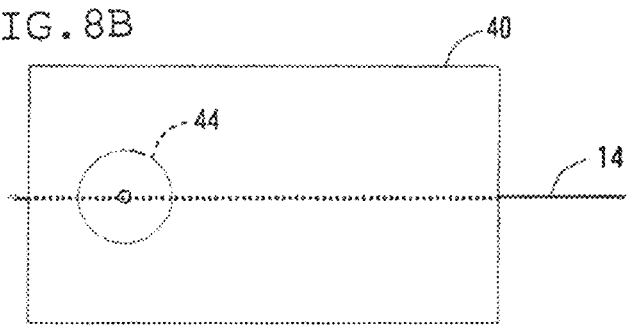
FIG. 8B is a bottom view.

Then, the process proceeds to step 180, where as shown in FIG. 8, an electrode (for example, platinum electrode) 60 is inserted into the electrode insertion hole 52 to complete a spray device. The drawing shows an adhesive 54 for securing the reservoir 50 to the insulating plate 40.

As the adhesives 46 and 54, it is possible to employ those, which are not altered by the electrophoretic liquid used for CE-MS, such as a silylated urethane resin, a cyanoacrylate resin, or a urethane resin.

Figure 9:
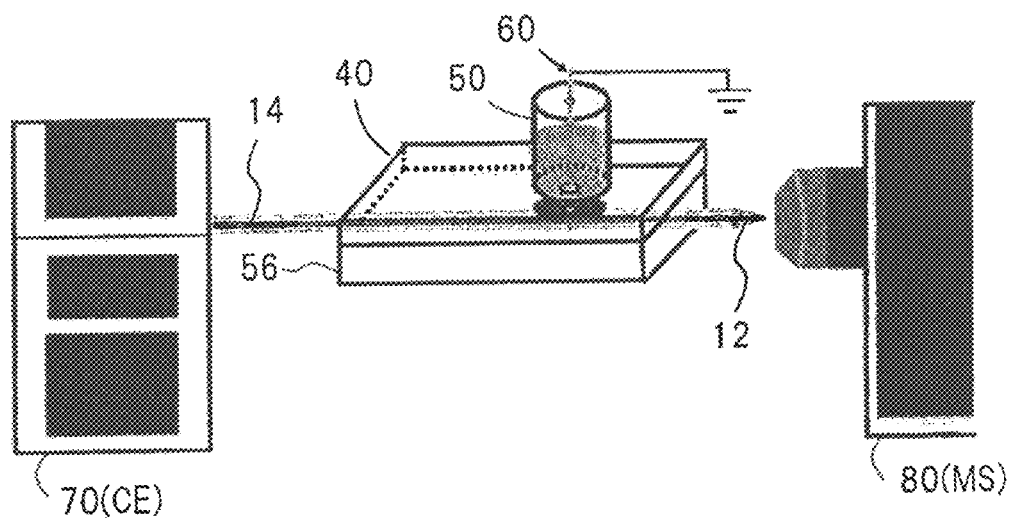
FIG. 9 is a schematic view illustrating the entire configuration of a CE-MS device to which an embodiment of the present invention has been applied.

FIG. 9 shows a sheathless CE-MS device configured by connecting the completed spray device between the CE 70 and the MS 80. The drawing shows a base plate 56.

The sheathless CE-MS device shown in FIG. 9 was used to make measurements. Cationic metabolite measurement conditions are as below (see Non-Patent Literatures 6 and 7).

(i) Analysis Conditions for Capillary Electrophoresis (CE)

As the capillary 14, it is possible to employ a fused silica capillary of various inner diameters (for example, an inner diameter of 50 μm and an outer diameter of 360 μm). The buffer liquid 16 employed was 10% (v/v) acetic acid (about a pH of 2.2). The measurements were made at the applied voltage +30 kV, and the capillary temperature was 20° C. The sample was injected for 15 seconds at 50 mbar by the pressurizing method.

(ii) Analysis Conditions for the Time-of-Flight Mass Spectrometer (TOFMS)

In the positive ion mode, the ionization voltage was set to 1.8 kV, the flag mentor voltage to 175 V, the skimmer voltage to 50 V, and the OctRF voltage to 100 V. The drying gas employed was nitrogen, and the temperature was set to 300° C. Measurements were made on compounds of a mass to charge ratio (m/z) of 50 to 1,000 at a scan speed of 1.5 cycles/second.

(iii) Analysis Conditions for Triple Quadrupole Mass Spectrometer (QqQMS)

In the positive ion mode, the ionization voltage was set to 2.4 kV, and the flag mentor voltage to 90 V. The drying gas employed was nitrogen, and the temperature was set to 300° C. By the multiple reaction monitoring (MRM) method, measurements were made at the optimized precursor m/z, product m/z, and collision energy for each compound name.

Figure 10:
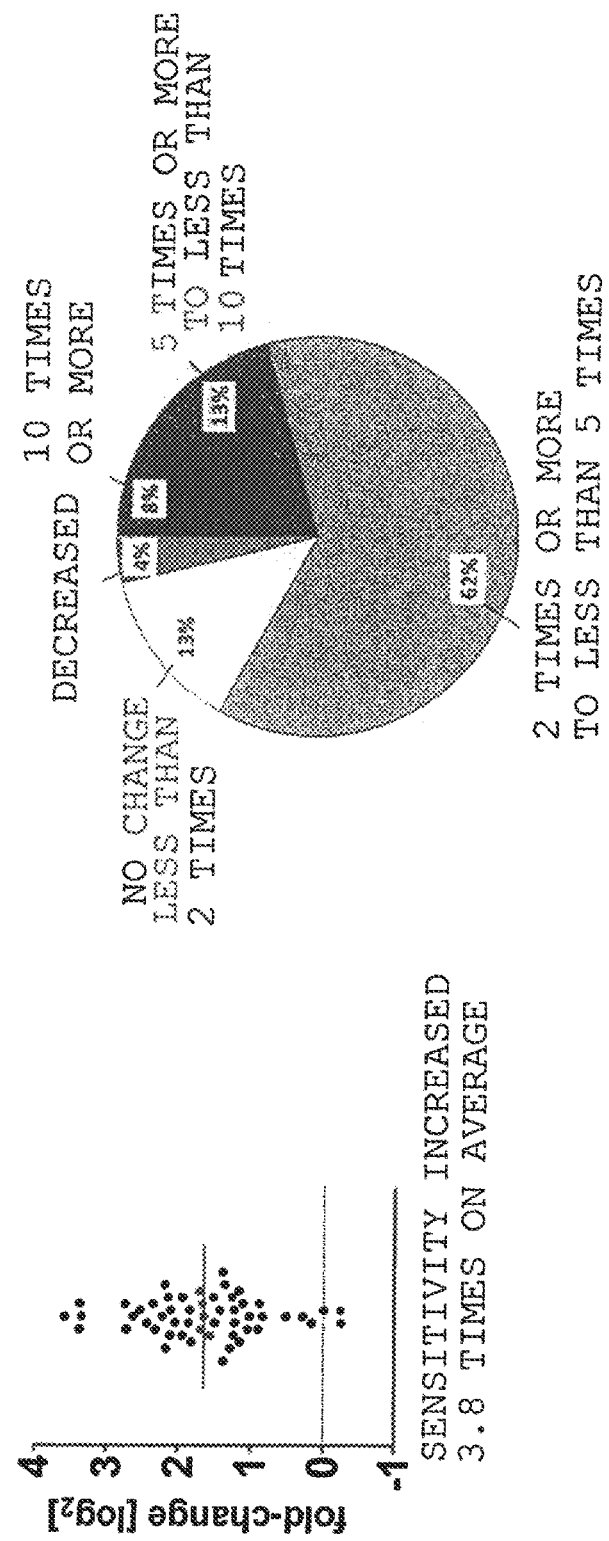
FIG. 10 is a view illustrating the result of a comparison made in sensitivity between a created sheathless CE-MS device connected to a time-of-flight mass spectrometer (TOFMS) and a conventional sheath flow TOFMS.

The created sheathless CE-MS device was connected to TOFMS to make a comparison in sensitivity with a conventional sheath flow TOFMS, of which results are shown in FIG. 10.

As a result of measuring 53 types of cationic metabolite standard solutions, 83% (45/54) compounds were found to have increased in sensitivity by two times or more, and an average increase in sensitivity of 3.8 times was achieved. Note that the sensitivity was decreased for hypoxanthine and spermidine, but this is thought to be because of an increase in background noise due to the electrophoretic liquid. It is thus possible to readily accommodate the degradation by changing the type of electrophoretic liquids.

Figure 11:
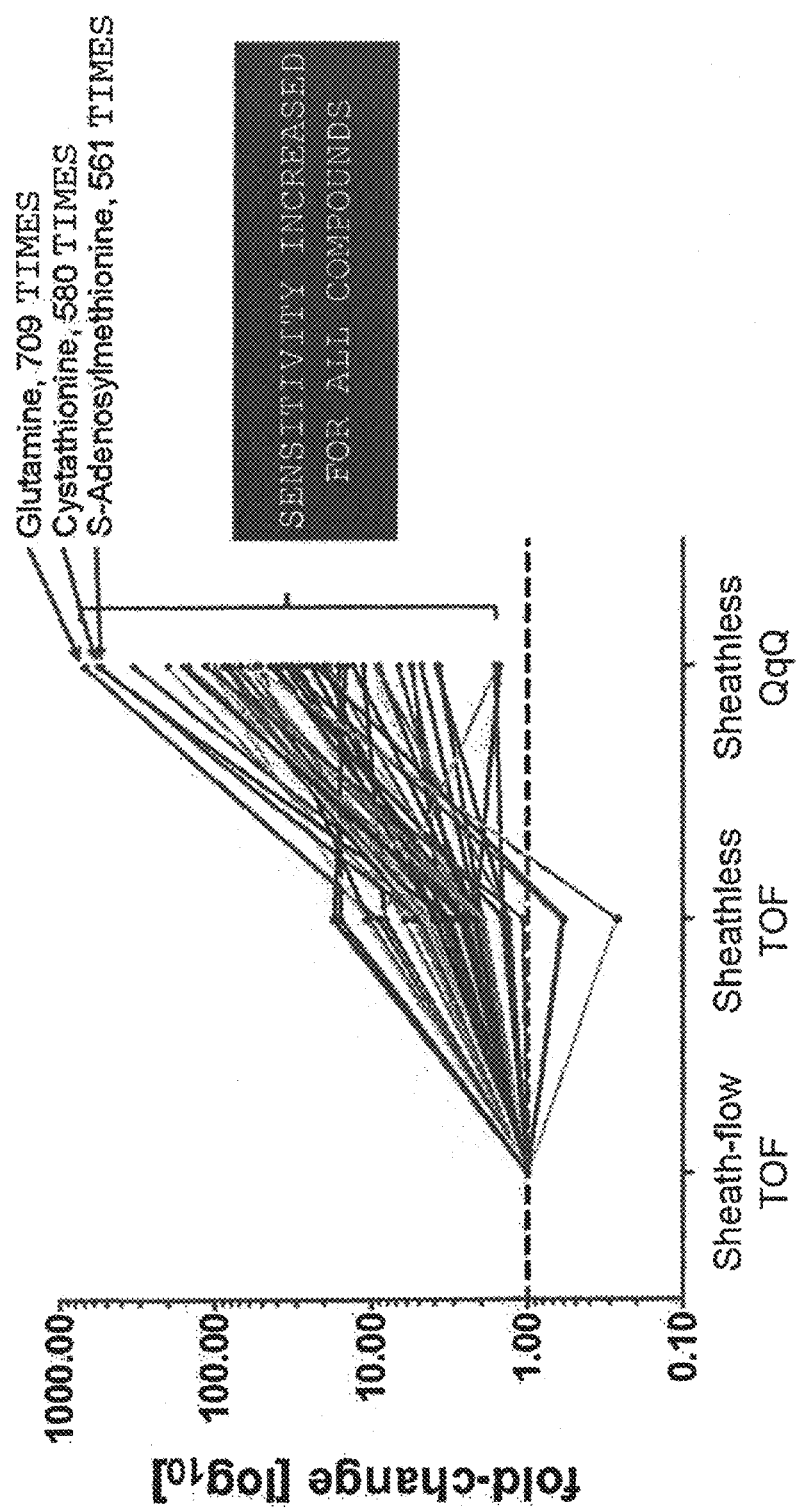
FIG. 11 is a view also illustrating the result of a comparison made in sensitivity between the sheathless TOFMS shown in FIG. 10 connected to a triple quadrupole mass spectrometer (QqQMS) and a conventional sheath flow TOFMS.

Furthermore, the sheathless CE-MS device was connected to QqQMS to make a comparison in sensitivity between the conventional sheath flow TOFMS and the sheathless TOFMS shown in FIG. 10, of which results are shown in FIG. 11.

In this case, as compared with the sheath flow TOFMS, the sensitivity was increased for all compounds, so that high sensitivities, such as 709 times for glutamine, 580 times for cystathionine, and 561 times for S-adenosylmethionine, were achieved.

INDUSTRIAL APPLICABILITY

It is possible to provide a CE-MS device that is capable of measuring compounds with high sensitivity.

REFERENCE SIGNS LIST

10 spray
12 needle
14 capillary
16 electrophoretic (buffer) liquid
40 insulating plate
42 electrophoretic liquid passing hole
44 electrodialysis membrane
46, 54 adhesive
48 crack
50 reservoir
52 electrode insertion hole
60 electrode

The invention claimed is:

1. A method of creating a spray device for sheathless CE-MS, the method comprising:
    a step of processing a distal end of a capillary to have an acute angle;
    a step of opening an electrophoretic liquid passing hole, through which an electrophoretic liquid can pass, in a flexible insulating plate;
    a step of bonding an electrodialysis membrane so as to cover the electrophoretic liquid passing hole;
    a step of securely bonding the capillary to a portion of the insulating plate with no gap therebetween, the portion excluding the electrophoretic liquid passing hole on top of the electrodialysis membrane;
    a step of forming a crack at a portion of the capillary at the electrophoretic liquid passing hole, the capillary being entirely secured to the insulating plate except a portion at the electrophoretic liquid passing hole;
    a step of entirely securely bonding the capillary to the insulating plate;
    a step of placing a reservoir for storing the electrophoretic liquid on a side of the insulating plate to which the capillary is not secured;
    a step of opening an electrode insertion hole, into which an electrode is inserted, in an upper portion of the reservoir; and
    a step of inserting and securing the electrode into the electrode insertion hole.

2. The method of creating a spray device for sheathless CE-MS according to claim 1, wherein
    the step of forming the crack includes:
        a step of scratching, with a cutter, a surface of the portion of the capillary at the electrophoretic liquid passing hole; and
        a step of deflecting the insulating plate to bend the capillary, thereby forming a crack at the portion at the electrophoretic liquid passing hole.

3. The method of creating a spray device for sheathless CE-MS according to claim 1, wherein the insulating plate is a plastic plate or a glass plate.

4. The method of creating a spray device for sheathless CE-MS according to claim 1, wherein the electrodialysis membrane is an ion exchange membrane.

5. The method of creating a spray device for sheathless CE-MS according to claim 1, wherein the reservoir is made of an insulator.

6. The method of creating a spray device for sheathless CE-MS according to claim 2, wherein the cutter is a ceramic cutter.

7. A spray device for sheathless CE-MS, the spray device comprising:
- a capillary with a distal end processed to have an acute angle and with a crack formed at an intermediate portion;
- an insulating plate to which the capillary is securely bonded and in which an electrophoretic liquid passing hole for enabling an electrophoretic liquid to pass therethrough is formed at a portion having the crack formed;
- an electrodialysis membrane bonded onto the electrophoretic liquid passing hole of the insulating plate;
- a reservoir which is placed on a side of the insulating plate having the capillary not secured thereto and which stores the electrophoretic liquid; and
- an electrode which is inserted and secured to an upper portion of the reservoir.

8. A sheathless CE-MS device comprising the spray device according to claim 7.

9. The method of creating a spray device for sheathless CE-MS according to claim 2, wherein the insulating plate is a plastic plate or a glass plate.

\* \* \* \* \*